United States Patent [19]
Jimenez et al.

[11] Patent Number: 5,242,800
[45] Date of Patent: Sep. 7, 1993

[54] RECEPTOR FOR PATHOGENIC FUNGI

[75] Inventors: Victor E. Jimenez; Victor Ginsburg, both of Bethesda; Howard C. Krivan, Rockville, all of Md.

[73] Assignee: The United States of America as represented by the Secretary of the Department of Health and Human Services, Washington, D.C.

[21] Appl. No.: 472,128

[22] Filed: Jan. 30, 1990

[51] Int. Cl.$^5$ .................... G01N 33/53; G01N 33/569
[52] U.S. Cl. .................... 435/7.2; 435/7.21; 435/7.31; 435/29; 435/32; 435/911; 436/501; 436/827; 514/25
[58] Field of Search .......... 436/501, 503, 827; 435/7.2, 7.21, 911, 29, 32, 7.31; 514/25, 54, 59

[56] References Cited

PUBLICATIONS

Slomiany, B. L., et al., *Biochemistry International*, vol. 19, No. 4, pp. 929–936 (1989).
Calander, N., et al., *Biochimie*, vol. 70, pp. 1673–1682 (1988).
Stromberg, N., et al., *Proc. Nat. Acad. Sci., U.S.A.*, vol. 85, pp. 4902–4906 (Jul., 1988).

*Primary Examiner*—Esther L. Kepplinger
*Assistant Examiner*—Toni R. Scheiner
*Attorney, Agent, or Firm*—Foley & Lardner

[57] ABSTRACT

A glycolipid receptor that specifically binds pathogenic fungi has been identified. Various properties and utilities of the receptor have been described.

6 Claims, 5 Drawing Sheets

FIG. 5A
FIG. 5B
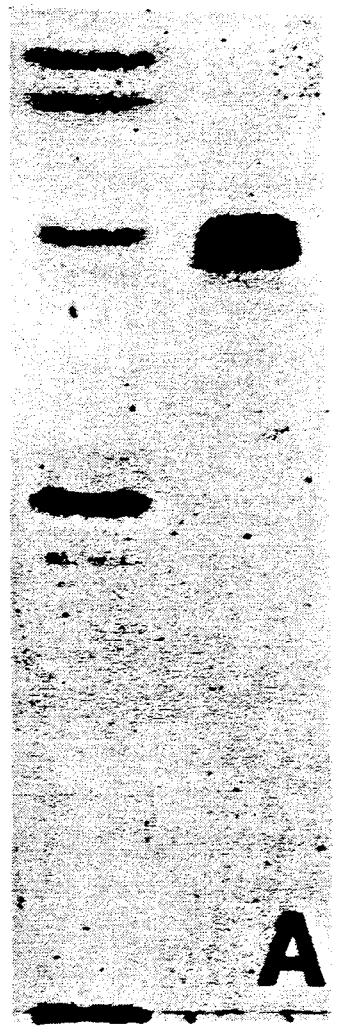
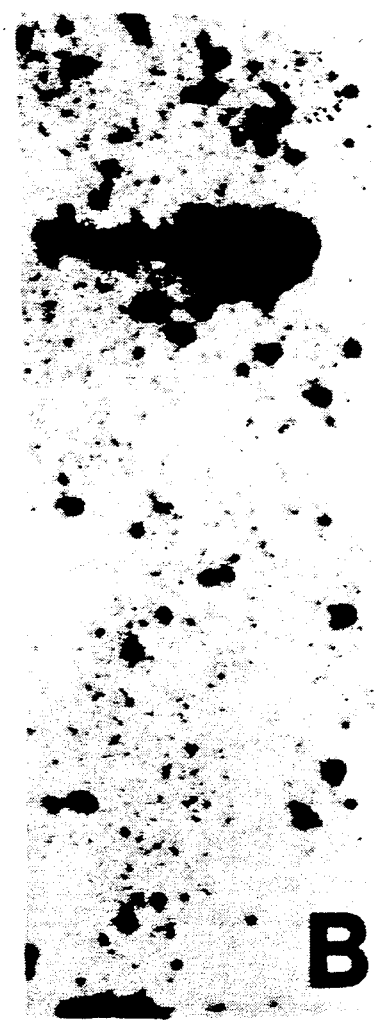
1  2     1  2

RECEPTOR FOR PATHOGENIC FUNGI

The present invention is related to the identification of a receptor that specifically binds pathogenic fungi. More particularly, the present invention is related to a specific glycolipid which comprises the carbohydrate sequence galactose β1-4 glucose linked to a ceramide (Galβ1-4Glcβ1-1Cer) and which has specific binding affinity for a plurality of fungi including *Candida albicans* and *Cryptococcus neoformans*.

BACKGROUND OF THE INVENTION

*Cryptococcus neoformans* are pathogenic fungi associated with several infectious diseases that afflict both humans and animals. Certain glycolipids are reported to be involved in the initial bacterial adhesion to host tissues (Krivan et al, 1988, *Proc. Natl. Acad. Sci. USA* 85:6157-61). However, specific receptors for pathogenic fungi including Candida and Cryptococcus have not heretofore been known or described.

SUMMARY OF THE INVENTION

It is, therefore, an object of the present invention to identify specific epitopes and/or receptors to which pathogenic fungi bind.

It is another object of the present invention to provide synthetic analogues that inhibit yeast adhesion to host tissues.

It is a further object of the present invention to provide a method for preventing infection and/or disease caused by pathogenic fungi.

It is an additional object of the present invention to provide a method for isolating purified components from the yeast cell that mediate yeast attachment to host cells.

It is yet another object of the present invention to provide a kit for detecting the presence of pathogenic fungi.

It is a still further object of the present invention to provide a composition comprising an effective amount of the fungal receptor for preventing or treating diseases caused by fungal infection, and a pharmaceutically acceptable carrier.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 5A and 5B demonstrate the binding of C.neoformans to neutral glycosphingolipids from human glioma cells. Neutral glycosphingolipids from 100 mg wet weight of human brain cells (lane 1) and 1 ug of bovine brain lactosylceramide (lane 2) were visualized with orcinol reagent (A) or overlayed with $^{125}$I-labeled cryptococci followed by autoradiography (B).

DETAILED DESCRIPTION OF THE INVENTION

Figure 1A:
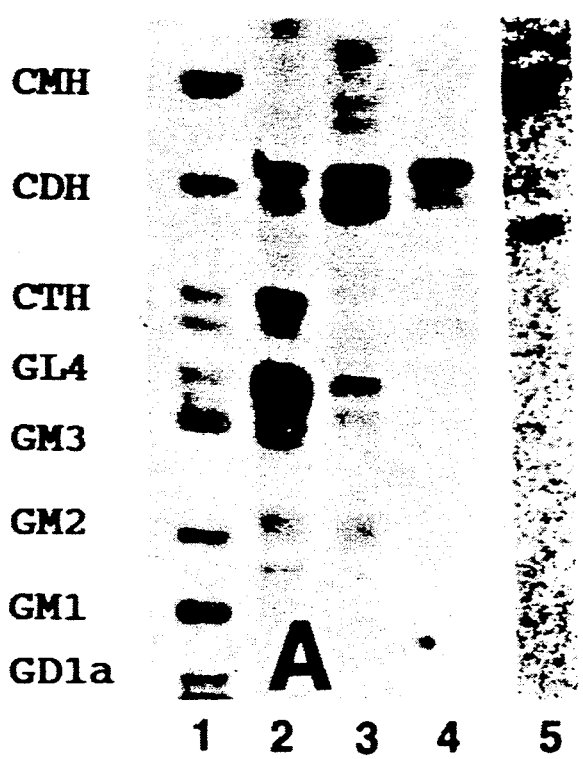
FIGS. 1A and 1B demonstrate the binding of *C. neoformans* to glycolipids on thin-layer plates. Glycosphingolipids were extracted and chromatographed in duplicate high performance thin-layer plates. The chromatograms were sprayed with orcinol reagent for glycolipid detection (A) or overlayed with $^{125}$I-labeled cryptococci followed by autoradiography (B). Lane 1, 2 ug galactosylcermide (CMH), 1 ug chemically synthesized lactosylceramide (CDH), 1 ug trihexosylceramide (CTH), 1 ug globoside (GL4) and 2 ug each of GM3, GM2, GM1 and GD1a; lane 2, neutral glycosphingolipids from 100 mg wet weight of human lung tissue; lane 3, neutral glycolipid fractions from $2 \times 10^6$ polymorphonuclear cells; lane 4, authentic lactosylceramide (1 μg); lane 5, hydrolysate of lactosylceramide treated with beta-galactosidase.

The above and various other objects and advantages of the present invention are achieved by (1) providing an isolated, substantially pure glycolipid receptor having specific binding affinity for pathogenic fungi; (2) a method for preventing infection of said pathogenic fungi and (3) a kit for detecting the presence of said pathogenic fungi.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "substantially pure" as used herein means as pure as can be obtained by standard isolation and purification means.

MATERIALS AND METHODS

It is noted that the materials and methods employed for the studies and tests related to various fungi are similar. Hence, the present invention is being illustrated herein employing only *Cryptococcus neoformans* as an example. Glycosphingolipids.

Galactosylceramide, glucosylceramide, globoside, trihexosylceramide and sulfatide were purchased from Supelco (Bellefonte, Pa.). Bovine brain lactosylceramide was obtained from Sigma (St. Louis, Mo.). Bovine erythrocyte lactosylceramide was obtained from Dr. M. Kyogashima (National Institutes of Health). Chemically synthesized lactosylceramide (DL-dihydrolactocerebroside) was from Calbiochem-Behring (San Diego, Calif.). Ganglioside standards were from Bachem (Torrence, Calif.). Gangliotetraosylceramide, gangliotriaosylceramide, and paragloboside were prepared as described by Krivan et al (1988, *Proc. Natl. Acad. Sci., U.S.A.* 85:6157) and Kyogashima et al (1989, *Arch. Biochem. Biophys.* 270:391). Lipids from normal human lung and human polymorphonuclear leukocytes were extracted and separated into neutral and acidic fractions by anion exchange chromatography on DEAE-sepharose (Pharmacia) in the bicarbonate form, as described by Krivan et al, supra. Human glioma brain cells were extracted as above, phase-partitioned (Folch et al, 1957, *J. Biol. Chem.* 226:497), and subjected to silicic acid chromatography (Biosil, BioRad) (Vance and Sweeley, 1967, *J. Lip. Res.* 8:621). Glucosylceramide was prepared from bovine erythrocyte lactosylceramide by treatment with bovine testes β-galactosidase as described by Krivan et al, supra. Polar contaminants and detergent were removed by Sephadex G-25 and DEAE-Sepharose column chromatography as described by Krivan et al, supra, and Magnani et al (1982, *Methods Enxymol.* 83:235). Liposomes containing glycosphingolipids were prepared as follows: One mg of lactosylceramide or galactosylceramide was added to cholesterol and phosphatidylcholine in a ratio of 3:2:4 by weight. The lipids were mixed in 1:1 $CHCl_3/CH_3OH$, dried under nitrogen, and sonicated 5 min in PBS. The liposomes were centrifuged at 4° C. and 10,000 g for 10 min and pellets were washed twice with PBS and resuspended to 1 mg glycosphingolipid/ml PBS.

Growth and Labeling of Fungi

The strains used in this study are listed in Table II. All fungi were grown in yeast nitrogen base medium (Difco) with 1% dextrose (Baker) without shaking at 26° C. or 37° C. with the exception of the dimorphic fungi *H. capsulatum* and *S. schenckii*, which were grown only at 37° C. as required for production of the yeast phase (Rippon, 1982, *Medical Mycology*, 2nd edition, W. B. Saunders Co., Philadelphia, Pa. pp. 532). After 2 to 7 days of growth, yeasts were harvested, washed twice by centrifugation (1000×g for 10 min) in phosphate-buffered saline (PBS, 0.01M sodium phosphate, pH 7.2, containing 0.15M sodium chloride), and suspended to $2 \times 10^8$ cells/ml PBS. Yeasts were radioiodinated as described for bacteria (Krivan et al, supra) with minor modifications. Briefly, 0.5 ml of the fungal suspension were reacted with 1 mCi of $Na^{125}I$ at 4° C. in a 10×75 mm tube coated with 100 μg of Iodogen. After 5 min, the suspension was transferred to a tube containing 0.5 ml of Hanks' Balanced Salt Solution[1] (HBSS-BSA, containing 1% bovine serum albumin, pH 7.4), washed by centrifugation (1000×g, 10 sec) and resuspended to $10^6$–$10^7$ cpm/ml HBSS-BSA. Expression of the *C. albicans* hyphal phenotype was obtained after incubating the yeasts in RPMI 1640 (Gibco) for 2 h at 37° C. in 5% $CO_2$ (Rippon, supra). For some tests, yeasts were fixed with 0.5% glutaraldehyde in PBS at 0° C. for 10 min and then washed with PBS.

Chromatogram Overlay Assay for Binding of Fungi to Glycosphingolipids

The chromatogram overlay assay was performed as used for bacteria (Hansson et al, 1985, *Anal. Biochem.* 146:158, and Krivan et al, supra). Briefly, glycosphingolipids were chromatographed on aluminum-backed silica gel highperformance thin layer plates (Merck, West Germany) developed with chloroform:methanol:0.25% aqueous KCl (5:4:1). The plates were coated with polyisobutylmethacrylate (0.1% in hexane), air-dried, soaked for 1 h in Tris-BSA buffer (0.05M Tris-HCl, pH 7.8, containing 0.15M sodium chloride and 1% bovine serum albumin), and overlayed for 3 h at room temperature (22°–24° C.) with $^{125}I$-labeled fungi ($2 \times 10^6$ cpm/ml HBSS-BSA). The plates were gently washed to remove unbound organisms, dried, and exposed 24 h to XAR-5 X-ray film (Eastman Kodak, Rochester, N.Y.).

Solid Phase Assay for Binding of Fungi to Glycosphingolipids

The solid phase binding assay was performed as described for bacteria (Krivan et al, supra). Briefly, serial dilutions of purified glycosphingolipids in methanol (25 μl) containing cholesterol and phosphatidylcholine (0.1 μg each) were added to polyvinylchloride microtiter wells (Falcon 3912-111, Becton, Dickinson) and dried by evaporation. The wells were blocked with Tris-BSA for 1 h, rinsed with HBSS-BSA twice, and incubated with 25 μl $^{125}I$-labeled yeast ($10^7$ cpm/ml HBSS) for 3 h at 25° C. After washing the wells five times with PBS, binding was quantified in a gamma spectrometer.

fungal Adhesion to Cultured Human Glioma Cells

Human glioma brain cells (ATCC HTB 238) were grown in Dulbecco's Modified Eagle's medium supplemented with 10% fetal calf serum at 37° C. in 5% $CO_2$-95% air. Cells were grown until they formed confluent monolayers, usually 7 days, on round coverslips (13 mm diam.) placed in 24-well tissue culture plates. For some tests, cells were fixed in 0.5% glutaraldehyde at 4° C. for 1 h. The wells were washed with serum-free medium and then incubated with 1 ml $^{125}I$-labeled fungi ($2 \times 10^6$ cpm/ml HBSS). After incubation for the indicated period, the coverslips were washed five times with PBS and the bound radioactivity was measured. For inhibition tests the fungi were preincubated for 1 h at 25° C. with liposomes or free sugars.

RESULTS

Figure 1B:
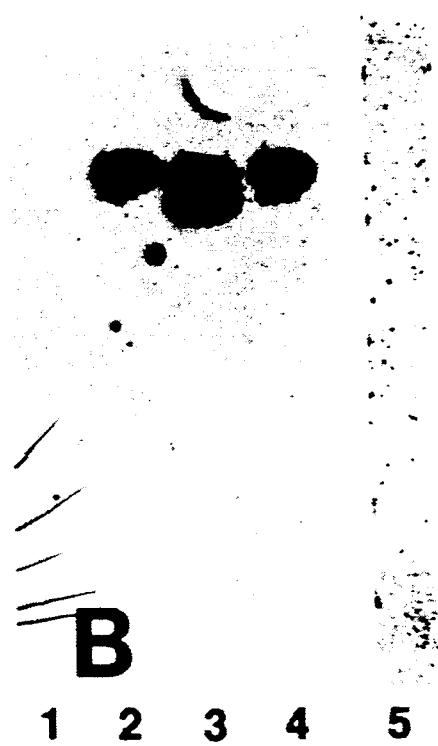
Figure 2A:
FIGS. 2A and 2B demonstrate the binding of *C. neoformans* to various concentrations of lactosylceramide. Various concentrations of purified bovine red blood cell lactosylceramide on duplicate thin-layer chromatograms were visualized with orcinol reagent (A) or treated for binding to radiolabeled $^{125}$-cryptococci followed by autoradiography (B) as described in FIG. 1. Lane 1, lactosylceramide 0.5 μg; lane 2, 0.35 μg; lane 3, 0.25 μg; lane 4, 0.15 μg; lane 5, 0.05 μg.
Figure 2B:

Binding of C. neoformans and other fungi to glycosphingolipids on chromatograms The binding of $^{125}I$-labeled *C. neoformans* to glycosphingolipids from normal human lung and human polymorphonuclear leukocytes was examined by the chromatogram overlay assay. As shown by autoradiography of the chromatogram (FIG. 1B) compared to an identical chromatogram of glycosphingolipids detected by orcinol reagent (FIG. 1A), the organisms bound to bovine erythrocyte lactosylceramide (FIG. 1, lane 4) and to glycosphingolipids with the same mobility from human lung (FIG. 1, lane 2) and human polymorphonuclear cells (FIG. 1, lane 3). That these glycosphingolipids were indeed lactosylceramide was shown by their specific immunostaining (Magnani et al, supra) with the monoclonal antibody $A_5T_7$, which is directed against lactosylceramide (Symington et al, 1984, *J. Biol. Chem.* 259:6008) (data now shown. It is noted that no binding was detected to synthetic lactosylceramide (DL-dihydrolactocerebroside) (FIG. 1, lane 1). Also, while binding was better to the upper band than to the lower band of the lactosylceramide doublet obtained from human lung (FIG. 1, lane 2) and bovine erythrocytes (FIG. 2, lane 4), binding was the same for both bands of lactosylceramide from human polymorphonuclear cells (FIG. 1, lane 3). The cryptococci did not bind to glucosylceramide derived from lactosylceramide by treatment with β-galactosidase (FIG. 1, lane 5), or to other neutral or acidic glycosphingolipids that were tested (FIG. 1, lane 1 and Table I). Lactosylceramide from bovine erythrocytes separates chromatographically into approximately equal amounts of upper and lower bands (FIG. 2A). The ceramide moiety in the upper band contains predominantly C24:0, C24:1 and C22:0 fatty acids, and in the lower band contains predominantly C16:0 and C18:0 fatty acids (Uemura et al, 1978, *J. Biochem.* 83:463). As is the case with lactosylceramide from human lung and bovine erythrocytes (FIG. 1, lanes 2 and 4), *C. neoformans* bound better to the upper band than to the lower band (FIG. 2B). Less than 25 ng of upper band lactosylceramide was detected (FIG. 2B).

The fungi that bind to lactosylceramide in the chromatogram overlay assay are listed in Table II. Binding was detected with the yeast phase of *C. albicans*, but not with the pseudohyphae phase. Also the dimorphic fungi *H. capsulatum* and *S. schenckii* in their yeast phase bound to lactosylceramide, as did the yeast *S. cerevisae* (data not shown).

Binding of *C. neoformans* to lactosylceramide immobilized in microtiter wells

Figure 3A:
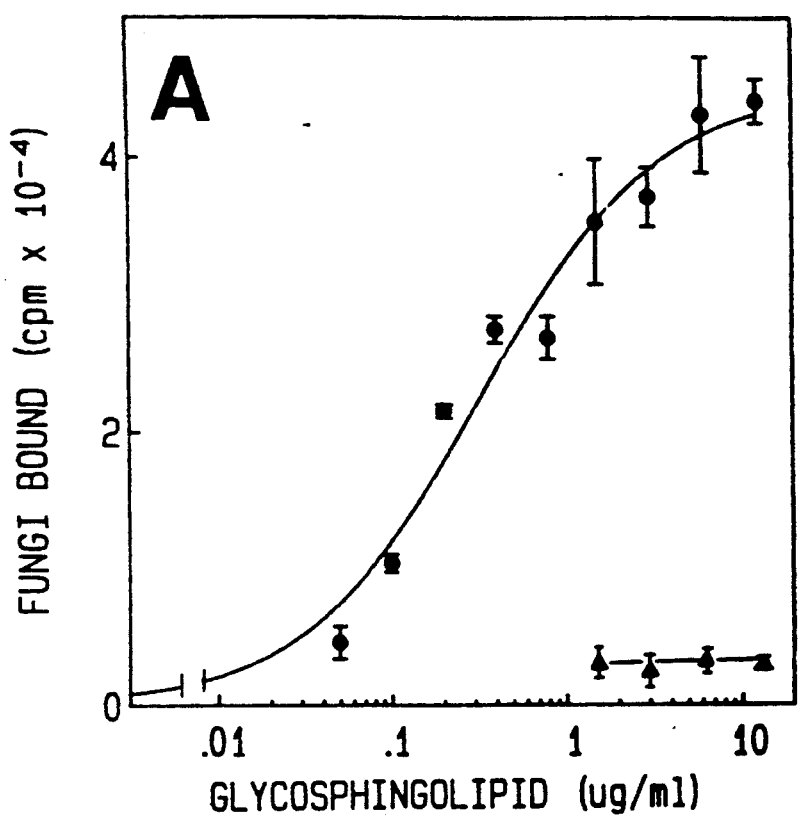
FIGS. 3A, 3B and 3C demonstrate the binding of *C. neoformans* to glycosphingolipids in solid phase assay. (A) Binding of 125I-labeled *C. neoformans* serial dilutions of purified glycosphingolipids in microtiter plates (3 h at 25 C.). Lactosylceramide(●); and asialo-GM1 or asialo-GM2(▲). (B) Binding of 125I-labeled C.neoformans r30serial dilutions of lactosylceramide in Tris/-BSA buffer(▲); Tris/BSA buffer supplemented with 5 mM Ca2+ amd Mg2+ (▲); Tris/BSA buffer supplemented with 2 mM glucose (○); in HBSS medium (■); and in HBSS medium containing 10 nM EDTA/EGTA (●). Percent binding is relative to the maximal amount bound. (C) Inhibition of binding by lyposomes containing glycosphingolipids. Binding of 125I-labeled *C. neoformans* to 1 μg lactosylceramide was determined after incubation of the fungi for 1 hour at 25 C. with the indicated concentrations of liposomes containing lactosylceramide (●) or glycosylceramide, (▲).
Figure 3B:
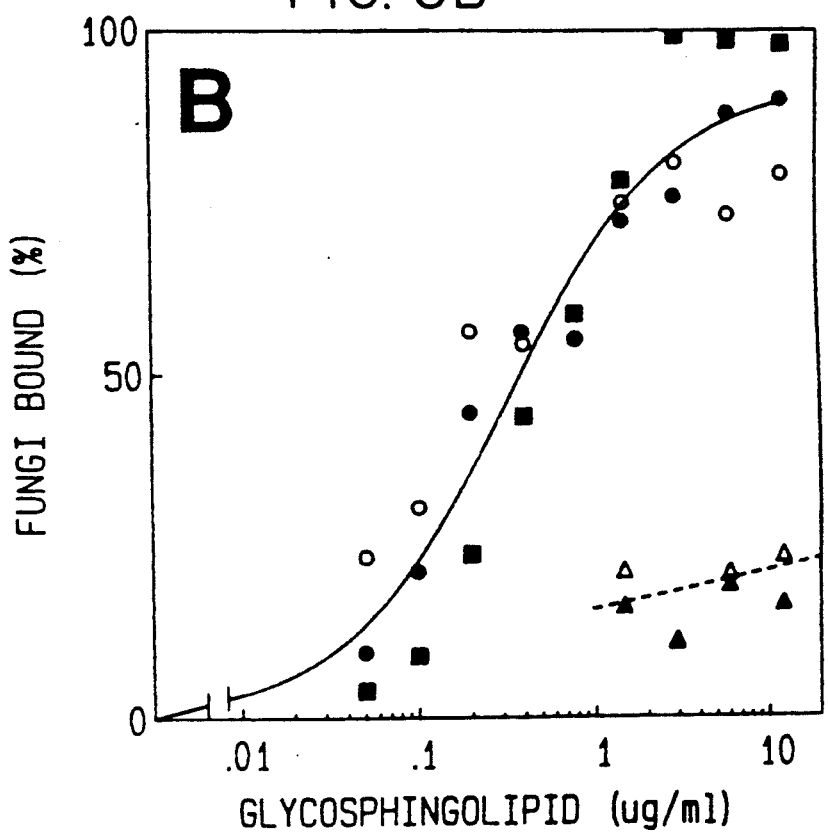

The binding of *C. neoformans* to lactosylceramide by solid phase assay was measured (FIG. 3A). Binding was concentration-dependent and half-maximal binding required about 0.2 μg of lactosylceramide per well. No binding was detected to asialo-GM1 or asialo-GM2. The effect of yeast viability and growth on binding was also examined (FIG. 3B). Fungi suspended in Tris-BSA buffer alone did not bind, but binding was restored by the addition of glucose to the buffer. The absence of $Ca^{2+}$ and $Mg^{2+}$ in the incubation medium or the addition of the chelating agents EGTA/EDTA had no affect. Glutaraldehyde-fixed yeasts did not bind to lactosylceramide (data not shown).

Figure 3C:
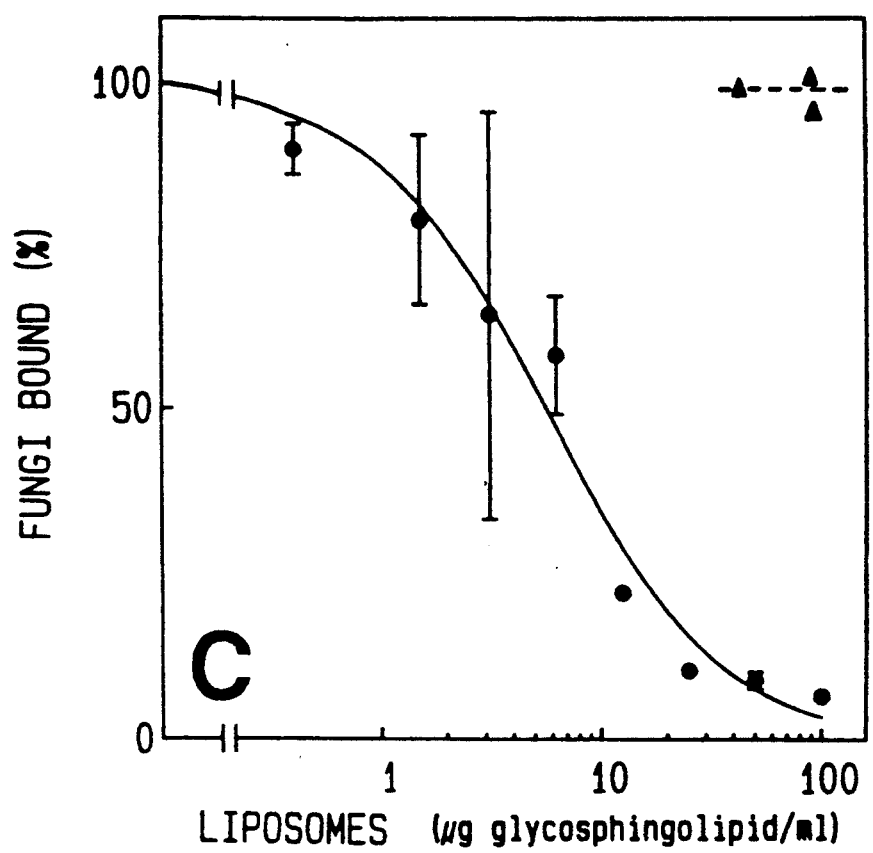

The specificity of binding of *C. neoformans* to lactosylceramide was further defined by inhibition experiments using liposomes containing glycosphingolipids (FIG. 3C). Liposomes containing lactosylceramide, but not glucosylceramide, inhibited binding. About 6 μg/ml of lactosylceramide inhibited binding by 50% whereas glycosylceramide at 100 μg/ml had no effect. Glucose, galactose, and lactose at 100 μg/ml did not inhibit binding (data not shown).

Adhesion of *C. neoformans* to human brain cells

Figure 4:
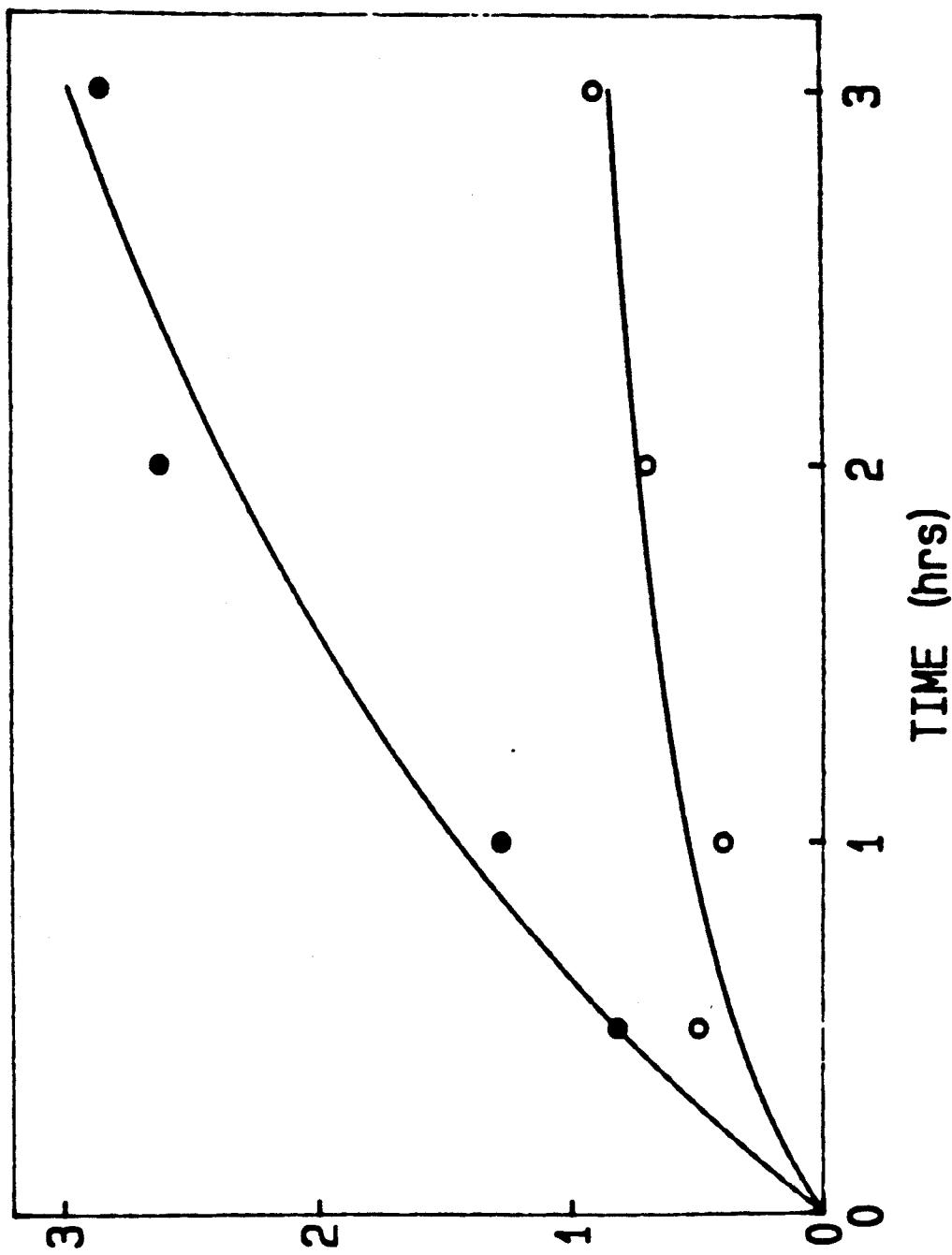
FIG. 4 demonstrates the adhesion of C.neoformans to human brain cells. Cultured glioma cell monolayers were incubated with $^{125}$I-labeled cryptococci for various times at 37° C. (●) or at 4° C. (○), and were washed free of excess cryptococci. The data is expressed as bound radioactivity per coverslip. Results represent the mean of quadruplicate samples.

Because brain is a common site of human cryptococcal infection, the adhesion of cryptococci to human glioma cells grown in monolayers was tested. $^{125}$I-labeled *C. neoformans* adhered readily to brain glioma cell monolayers and adhesion was both time- and temperature-dependent (FIG. 4). Adhesion was almost complete at 2 h, and was markedly reduced at 4° C. as compared to 37° C.

As was the case with the binding of *C. neoformans* to immobilized lactosylceramide (FIG. 3C), binding to glioma cells was strongly inhibited by liposomes containing lactosylceramide, whereas an equal amount of liposomes containing glucosylceramide had no effect (Table III). Glucose, galactose and lactose at 100 μg/ml did not effect binding (data not shown). *C. neoformans* bound as well to glutaraldehyde-fixed glioma cell monolayers as to unfixed monolayers (98% of control).

Lactosylceramide is a major glycosphingolipid in the glioma cell line as shown in FIG. 5A. $^{125}$I-labeled *C. neoformans* bound only to the glycosphingolipid in these cells that comigrated with authentic lactosylceramide (FIG. 5B).

In short, the data presented herein clearly show that *C. neoformans*, *C. albicans* and other yeasts bind specifically to lactosylceramide, as measured by overlay assay (FIGS. 1 and 5, and Table II) and solid phase assay (FIG. 3A). The terminal galactosyl residue of lactosylceramide is required for binding, as *C. neoformans* do not bind to glucosylceramide derived from bovine erythrocyte lactosylceramide by treatment with β-galactosidase (FIG. 1, lane 5). Substitution of the lactosyl residue with other sugars blocks binding as the evyptococci do not bind to asialo-GM1 or asialo-GM2, which are receptors for many bacterial lung pathogens (Krivan et al, supra) or to other glycosphingolipids with internal lactose sequences that were tested (FIGS. 1, 3A and 5, and Table I). Thus, the yeasts require an unsubstituted lactosyl residue for binding in contrast to bacteria such as *Neisseria gonorrhoea*, *Propionibacterium granulosum* and *Bordetella pertussis* (Stromberg et al, 1988, *Proc. Natl. Acad. Sci., USA* 85:4902; Stromberg et al, 1988, *FEBS* 232:193; and Tuomanen et al, 1988, *J. Exp. Med.* 168:267) which bind to lactosylceramide, but also bind to glycosphingolipids with internal lactosyl sequences.

The binding of *C. neoformans* to lactosylceramide is affected by the structure of the ceramide moiety as was previously shown with antibodies (Symington et al, supra) and bacteria (Stromberg et al, supra; and Kyogashima et al, supra). The cryptococci do not bind to chemically synthesized lactosylceramide and bind better to the upper band than to the lower band of the lactosylceramide doublet obtained from human lung and bovine erythrocytes (FIGS. 1 and 2). The upper band of bovine erythrocyte lactosylceramide contains longer fatty acids than does the lower band (Uemura et al, supra). Thus, *C. neoformans* binds better to lactosylceramide with long fatty acids than with short fatty acids, as do some bacteria (Stromberg et al, supra) and an antibody directed against lactosylceramide (Symington et al, supra).

*C. neoformans* also bind strongly to brain cells (FIG. 4), a major site of infection in man and animals (Rippon, supra; and Armstrong, 1981, In clinical approach to Infection in the compromised host, R. H. Rubin and L. S. Young, editors, Plenum Medical Book Co., New York, 195). Lactosylceramide is present in substantial amounts in brain cells and is the only glycosphingolipid to which the cryptococci bind (FIG. 5). Furthermore, the binding of C. neoformans to cultured human brain cells, and to lactosylceramide immobilized in microtiter wells, is strongly inhibited by liposomes containing lactosylceramide but not by liposomes containing glucosylceramide (Table III and FIG. 3C). Free lactose at the same concentration does not inhibit binding, probably because the binding of yeasts to liposomes containing lactosylceramide is multivalent and of high affinity whereas binding to lactose is monovalent and of low affinity, as is common with many other ligand receptor interactions (Dower et al., 1982, In Cell Surface Phenomena. C. de Lisi, F. W. Wiegel, and A. S. Perelson, editors. Marcel Dekker, New York).

Binding of yeasts require glucose but not divalent cations (FIG. 3B), and is temperature dependent (FIG. 4), suggesting that only metabolically active organisms adhere, as has been previously found for the adherence of bacteria to carbohydrate ligands (Krivan et al., supra; Krivan et al., 1989, J. Biol. Chem. 264:9283; and Yu et al., 1987, Biochem. and Biophys. Res. Communication, 149:86). Of note, sugar alone as a carbon source promotes adhesion of C. albicans yeasts by increasing the expression of surface fibrillar adhesions (Douglas, 1987, In The Yeasts. Vol 2. Yeasts and the Environment, A. H. Rose and J. S. Harrison, editors. Academic Press, New York, 239). Glutaraldehyde-fixed yeasts do not bind, while the unfixed organisms bind well to glutaraldehyde-fixed monolayers. This resembles the binding of lymphocytes to high-endothelial venules: lymphocytes bind to glutaraldehyde-fixed endothelium but glutaraldehyde-fixed lymphocytes no longer bind (Stamper and Woodruff, 1977, J. Immunol. 119:772). The activity of the carbohydrate-binding protein on lymphocytes is destroyed by glutaraldehyde whereas the carbohydrate receptor on the endothelium is unaffected (Yednock and Rosen, 1989, Adv. Immunol. 44:313).

The results indicate that the adhesion of various yeasts is similar since all species examined, including the yeast-phase (tissue invasive form) of the dimorphic fungi H. capsulatum and S. schenckii, bind to lactosylceramide (Table II). Without being bound to any specific theory, it is postulated that C. albicans' failure to bind to lactosylceramide after induction of the hyphal phase may reflect the inhibition in cell division and other functions that occur during this phase (Rippon, supra; Soll, 1985, Candida albicans. P. J. Szamilo, J. L. Harris, editors. Plenum Press, New York, pp. 167). Alternatively, phenotypic changes in cell wall components specific for this phase might be involved (Soll, supra). Although yeasts vary in their pathogenic potential, they all share the ability to colonize the host. While C. albicans and C. neoformans are the species most frequently causing disease in man, other opportunistic yeasts can cause severe disease in the immunocompromised patient (Rippon, supra; Sethi and Mandell, 1988, N.Y. State J. Med. 88:278). Similarly, the pathogenicity of several Cryptococcus species is the same when tested in immunosuppressed mice (de Bernarids et al, 1987, Microbiol. Immunol. 31:449). Thus, factors other than the ability to colonize the host tissues must account for the differences in pathogenicity among yeasts.

Taken together, the data presented herein indicate that lactosylceramide is a host receptor for yeast adhesion. Since all yeasts examined in this study bind to lactosylceramide, this property may be essential for other unknown fungal cell functions as well. Nevertheless, the ubiquity of this glycosphingolipid in mammalian tissues favors the potential of these organisms to colonize host tissues such as mucosas and lung, and may account for the multiple organ involvement in disseminated fungal disease.

Lactosylceramide being a major glycosphingolipid in these cells and the only one to which the yeasts bind, this glycosphingolipid appears to be the receptor for yeast colonization and disseminated disease in humans. Of course, given the chemical structure of the fungal receptor, analogues having properties similar to said receptor can now be easily made following standard methodologies well known in the art to which this invention belongs. A kit comprises a container containing the fungal receptor for detecting or inhibiting fungal infection.

It is understood that the examples and embodiments described herein are for illustrative purposes only and that various modifications or changes in light thereof will be suggested to persons skilled in the art and are to be included within the spirit and purview of this application and scope of the appended claims.

TABLE I

| Glycosphingolipid (abbreviation) | Structure |
|---|---|
| Galactosylceramide (CMH) | Gal$\beta$1-1Cer |
| Glucosylceramide | Glc$\beta$1-1Cer |
| Lactosylceramide (CDH) | Gal$\beta$1-4Glc$\beta$1-1Cer |
| Trihexosylceramide (CTH) | Gal$\alpha$1-4Gal$\beta$1-4Glc$\beta$1-1Cer |
| Paragloboside | Gal$\beta$1-4GlcNAc$\beta$1-3Gal$\beta$1-4Glc$\beta$1-1Cer |
| Globoside (GL4) | GalNAc$\beta$1-3Gal$\alpha$1-4Gal$\beta$B1-4Glc$\beta$1-1Cer |
| Gangliotetraoxylceramide (Asialo-GM1) | Gal$\beta$1-3GalNAc$\beta$1-4Gal$\beta$1-4Glc$\beta$1-1Cer |
| Gangliotriaosylceramide (Asialo-GM2) | GalNAc$\beta$1-4Gal$\beta$1-4Glc$\beta$1-1Cer |
| Sulfatide | Gal(3SO$_4$)$\beta$1-1Cer |
| GM3 | NeuAc$\alpha$2-3Gal$\beta$1-4Glc$\beta$1-1Cer |
| GM2 | GalNAc$\beta$1-4(NeuAc$\alpha$2-3)Gal$\beta$1-4Glc$\beta$1-1Cer |
| GM1 | Gal$\beta$1-3GalNAc$\beta$1-4(NeuAc$\alpha$2-3)Gal$\beta$1-4Glc$\beta$1-1Cer |
| GD1a | NeuAc$\alpha$2-3Gal$\beta$1-3GalNAc$\beta$1-4(NeuAc$\alpha$2-3)Gal$\beta$1-4Glc$\beta$1-1Cer |
| GD1b | Gal$\beta$1-3GalNAc$\beta$1-4(NeuAc$\alpha$2-8NeuAc$\alpha$2-3)Gal$\beta$1-4Glc$\beta$1-1Cer |
| GT1b | NeuAc$\alpha$2-3Gal$\beta$1-3GalNac$\beta$1-4(NeuAc$\alpha$2-8NeuAc$\alpha$2-3)Gal$\beta$1-4Glc$\beta$1-1Cer |

Structures of glycosphingolipids tested for binding of yeasts

TABLE II

Fungi that Bind to lactosylceramide[1]

| Fungi | Strain | Comments |
|---|---|---|
| Cryptococcus neoformans | ATCC 34877 | type culture |
| Cryptococcus neoformans | NIH 68A | type culture |
| Cryptococcus neoformans | IMT 43 | clinical isolate |
| Cryptococcus neoformans | HFH 32 | clinical isolate |
| Candida albicans[2] | ATCC 18804 | type culture |
| Candida albicans[2] | HFH 44 | clinical isolate |
| Candida albicans[2] | HFH 45 | clinical isolate |

TABLE II-continued

Fungi that Bind to lactosylceramide[1]

| Fungi | Strain | Comments |
|---|---|---|
| Histoplasma capsulatum[2] | CDC B923 | clinical isolate |
| Histoplasma capsulatum[2] | IMT 55 | clinical isolate |
| Sporotrichum schenckii[2] | CDC B4668 | clinical isolate |
| Sporotrichum schenckii[2] | IMT 58 | clinical isolate |
| Saccharomyces cerevisae | ATCC 18824 | type culture |
| Saccharomyces cerevisae | HFH 21 | clinical isolate |

[1]Determined by the chromatogram overlay assay using 1 μg of bovine erythrocyte lactosylceramide as described in Materials and Methods.
[2]Tested in the yeast-phase as described in Materials and Methods.

TABLE III

Inhibiton of the adhesion of *C. neoformans* to human brain cells by liposomes containing glycosphingolipids.

| Liposomes | Adhesion[1] % |
|---|---|
| Lactosylceramide | 16 |
| Galactosylceramide | 97 |

[1]Cryptococci were incubated for 1 h at 25° C. with liposomes (100 μg of glycosphingolipid/ml HBSS), and their adhesion to brain cell monolayers was testd as described in the legend to FIG. 4 after incubation for 3 h at 37° C. Percent adhesion is relative to that of fungi incubated for 1 h at 25° C. in HBSS without added lipsomes.

What is claimed is:

1. An in vitro method for inhibiting adhesion of a pathogenic fungus to a host cell, comprising the steps of
    (a) contacting a pathogenic fungus with an adhesion inhibiting concentration of lactosylceramide and
    (b) contacting said pathogenic fungus bound to said lactosylceramide with a host cell in vitro.

2. The method of claim 1, wherein said pathogenic fungus is selected from the group consisting of *Cryptococcus neoformans, Candida albicans, Histoplasma capsulatum, Sporotrichum schenckii* and *Saccharomyces cerevisae.*

3. An in vitro method for detecting the presence of a fungus in a biological sample, comprising the steps of
    (a) incubating a biological sample with lactosylceramide and
    (b) measuring a fungus which binds to said lactosylceramide.

4. The method of claim 3, wherein said fungus is selected from the group consisting of *Cryptococcus neoformans, Candida albicans, Histoplasma capsulatum, Sporotrichum schenckii* and *Saccharomyces cerevisae.*

5. A kit for assaying the presence of a fungus, said kit comprising
    (a) at least two receptacles containing bound lactosylceramide and
    (b) a fungus which is known to bind to said lactosylceramide and which serves as a positive control in an assay for the presence of a fungus.

6. An in vitro method of inhibiting adhesion of a pathogenic fungus to a host cell, comprising the steps of
    (a) coating said host cell with an abhesion inhibiting concentration of free lactosylceramide, and
    (b) exposing said host cell coated with said lactosylceramide to a pathogenic fungus, thereby permitting said pathogenic fungus to bind with said lactosylceramide but not with said host cell.

* * * * *